US007569060B2

(12) United States Patent
Faoro (10) Patent No.: US 7,569,060 B2
(45) Date of Patent: Aug. 4, 2009

(54) APPARATUS FOR THE FIXING OF THE POSITION OF BONE CUTS

(75) Inventor: Francisco Faoro, Zürich (CH)

(73) Assignee: Zimmer, GmbH, Winterthur (CH)

( * ) Notice: Subject to any disclaimer, the term of this patent is extended or adjusted under 35 U.S.C. 154(b) by 170 days.

(21) Appl. No.: 10/820,988

(22) Filed: Apr. 8, 2004

(65) Prior Publication Data

US 2004/0249385 A1    Dec. 9, 2004

(30) Foreign Application Priority Data

Apr. 25, 2003    (EP) .................................. 03009440

(51) Int. Cl.
A61B 17/56    (2006.01)
(52) U.S. Cl. ...................................................... 606/87
(58) Field of Classification Search ............. 606/86–88, 606/89, 96, 102, 79
See application file for complete search history.

(56) References Cited

U.S. PATENT DOCUMENTS

| | | | |
|---|---|---|---|
| 4,349,018 A | | 9/1982 | Chambers |
| 4,457,307 A | * | 7/1984 | Stillwell ....................... 606/88 |
| 4,759,350 A | * | 7/1988 | Dunn et al. ................... 606/82 |
| 4,938,762 A | * | 7/1990 | Wehrli ........................... 606/88 |
| 5,213,112 A | * | 5/1993 | Niwa et al. .................. 600/587 |
| 5,228,459 A | * | 7/1993 | Caspari et al. .............. 128/898 |
| 5,275,603 A | * | 1/1994 | Ferrante et al. ............... 606/86 |
| 5,342,367 A | | 8/1994 | Ferrante et al. |
| 5,364,401 A | * | 11/1994 | Ferrante et al. ............... 606/84 |
| 5,364,402 A | | 11/1994 | Mumme et al. |
| 5,451,228 A | * | 9/1995 | Johnson et al. ............... 606/86 |
| 5,611,802 A | * | 3/1997 | Samuelson et al. ........... 606/86 |
| 5,681,316 A | * | 10/1997 | DeOrio et al. ................ 606/88 |
| 5,749,876 A | * | 5/1998 | Duvillier et al. .............. 606/88 |
| 5,925,049 A | * | 7/1999 | Gustilo et al. ................. 606/82 |
| 6,013,081 A | * | 1/2000 | Burkinshaw et al. .......... 606/88 |
| 6,174,314 B1 | * | 1/2001 | Waddell ....................... 606/88 |
| 6,796,986 B2 | * | 9/2004 | Duffner ....................... 606/87 |

(Continued)

FOREIGN PATENT DOCUMENTS

DE    203 03 498 U1    8/2003

(Continued)

OTHER PUBLICATIONS

Translation of European Search Report Dated Oct. 6, 2003.

*Primary Examiner*—William H. Matthews
*Assistant Examiner*—Ann Schillinger
(74) *Attorney, Agent, or Firm*—Baker & Daniels LLP (57) ABSTRACT

The invention relates to an apparatus for the fixing of the position of bone cuts for the insertion of knee implants comprising at least one cutting template which can be coupled to a base element fixed to the bone in the region of a condyle and can be fixed to the base element, wherein the cutting jig defines, in the fixed state and in each case by means of a slot for a cutting tool, a first cutting plane with respect to the base element and a second cutting plane with respect to the first cutting plane, and wherein the orientation of the second cutting plane can be set relative to the first cutting plane when the cutting jig is coupled to the base part and the respect knee anatomy is taken into account.

5 Claims, 8 Drawing Sheets

U.S. PATENT DOCUMENTS

2005/0273115 A1 * 12/2005 Coon et al. .................. 606/88

FOREIGN PATENT DOCUMENTS

| EP | 0 709 061 A1 | 5/1996 |
| EP | 0 809 969 A2 | 12/1997 |
| FR | 2 679 766 | 2/1993 |
| WO | WO 01/66021 A1 | 9/2001 |
| WO | WO 01/85038 A1 | 11/2001 |

* cited by examiner

FIG. 7

APPARATUS FOR THE FIXING OF THE POSITION OF BONE CUTS

CROSS-REFERENCE TO RELATED APPLICATION

This application claims priority to EPO Patent Application No. 03 009 440.3 filed Apr. 25, 2003.

The invention relates to an apparatus for the fixing of the position of bone cuts for the insertion of knee implants.

When knee prostheses are inserted, the condyles of the tibia and of the femur must be prepared in order to create contact surfaces on the bone which ensure a defined position of the tibia and femur implants.

The contact surfaces are produced by cutting away bone material at the condyles. In this process, one endeavors to remove as little bone material as possible. Furthermore, care must be taken that the cut surfaces at the tibia and at the femur are correctly oriented relative to one another so that the tibia and femur implants can cooperate in a manner corresponding to the natural movement of the knee joint.

This is in particular difficult in uni-compartmental operations in which a knee prosthesis should be implanted either only in the medial compartment or only in the lateral compartment. No instruments have existed to date with which the bone cuts to be carried out for this purpose can be fixed with the desired accuracy both with respect to their position and orientation relative to the respective condyle and with respect to the cut depth, above all in the direction of lateral-medial.

It is the object of the invention to provide an apparatus of the initially named kind with which the position of bone cuts to be carried out on the respective condyle can be fixed in as simple and as reliable a manner as possible and with an accuracy which is as high as possible, wherein this should in particular take place while taking the respective anatomic relationships into account as much as possible.

This object is satisfied by the features of claim 1 and in particular in that the apparatus includes at least one cutting jig which can be coupled to a base element fixed to the bone in the region of a condyle and which can be fixed to the base element, with the cutting jig in the fixed state respectively defining—by means of a slot for a cutting tool—a first cutting plane with respect to the base element and a second cutting plane with respect to the first cutting plane, and with the orientation of the second cutting plane being adjustable relative to the first cutting plane, when the cutting jig is coupled to the base element and taking the respective knee anatomy into account.

The apparatus for the fixing of the position of bone cuts in accordance with the invention is preferably made for the fixing of the position of bone cuts on a tibial condyle as part of a uni-compartmental knee operation by which a tibia plateau is produced which is preferably defined by two cutting surfaces extending perpendicular to one another and onto which a tibia implant of the knee prosthesis can be mounted in the further course of the operation.

In the following, in the further explanation of the invention, reference is made only to its use in conjunction with a tibial condyle for the simplification of the representation.

The invention starts from a basis element which is fixed correctly with respect to the position and orientation in the region of a condyle to be treated and which only defines a plane, without the cut depth being defined in any direction in the plane or parallel to the plane.

A reference is available with this base element relative to which the first cutting plane is fixed by means of the set of instruments in accordance with the invention. It is possible in accordance with the invention to define a second cutting plane relative to said first cutting plane and to set the orientation of said cutting plane relative to the first cutting plane. This can take place in accordance with the invention while taking the respective knee anatomy into account. Consequently, the invention not only permits two cutting planes to be fixed directly with respect to the basis element and relative to one another, but moreover to take the anatomical circumstances of the respective knee into account in this process.

Preferred embodiments of the invention are recited in the dependent claims, in the description and in the drawing.

Provision is preferably made for the first cutting plane and the second cutting plane to extend perpendicular to one another.

Provision can furthermore be made in accordance with the invention for the orientation of the second cutting lane to be adjustable with the cutting jig movable relative to the base element. The cutting jig can hereby be moved relative to the base element and simultaneously the orientation of the second cutting plane changed, whereby the slots formed at the cutting jig can be ideally aligned in accordance with the respective anatomical circumstances of the knee before the cutting jig is fixed to the base element.

The cutting jig is preferably only movable parallel to the first cutting plane in the state still not fixed. The position and the orientation of the first cutting plane relative to the base element hereby do not change on the movement of the cutting jig relative to the base element. Provision can furthermore be made for the cutting jig to be movable only in a straight line relative to the base element. For this purpose, a guide groove can be formed at the base element by which the cutting jig is compulsorily guided at the base element.

In accordance with a further embodiment of the invention, it is proposed that the cutting jig has at least one guide for an abutment element which, in at least one of the cutting planes, forms an abutment for the cutting tool restricting the respective cut.

The cutting depth can hereby be bounded in the corresponding direction in a simple and secure manner such that unwanted damage to the bone is avoided. The surgeon can concentrate on the carrying out of the cut and does not need to keep an eye on the cutting depth since he can rely on the correctly positioned abutment element in this respect.

The guide for the abutment element can be made such that the abutment element lies on the line of intersection of the two cutting planes. The desired line of intersection of the two cutting planes can hereby be precisely fixed by means of the abutment element. In this process, a boundary is fixed for both cutting planes with only one single abutment element.

Provision can furthermore be made in accordance with the invention for the guide for the abutment element to be forcibly coupled to the slot defining the second cutting plane. When setting the orientation of the second cutting plane, the orientation of the abutment element is hereby simultaneously fixed, whereby the handling of the instrument in accordance with the invention is further simplified.

The guide can include a passage which is formed in the cutting jig and through which the abutment element can be inserted. This passage can simultaneously serve as a guide for a drill with which the bone is first pre-drilled in order to subsequently be able to insert the abutment element into the bone.

In a preferred embodiment of the invention, an adjustable probe device is provided to take the knee anatomy into account and can be compulsorily coupled to the slot of the cutting jig defining the second cutting plane, with it being possible to set a plurality of predetermined implant sizes by adjusting a probe relative to a base part coupled to the slot.

A coupling section can be provided for the coupling to the slot and the probe device can probe the position of the eminentia and of the cruciate ligament anchoring via the former in order to make the slot defining the second cutting plane fixable with a safety spacing.

The orientation of the second cutting plane can be set using such a probe device in dependence on the anatomical circumstances of the respective knee. The surgeon can determine the implant size best suited for the operation by changing the orientation of the second cutting plane with a simultaneous adjustment of the probe relative to the base part coupled to the slot.

Provision is in particular made in accordance with the invention for the slot defining the first cutting plane to be formed by an intermediate space present between the upper side of the base element and a side of the cutting jig facing the base element when the cutting jig is coupled to the base element. When making the first cut, the cutting tool is consequently guided between the base element and the cutting jig. The cutting tool can lie on the upper side of the base element in this process. A displacement of the cutting jig relative to the base element does not change anything in the orientation and in the position of the slot defining the first cutting plane.

In a further embodiment of the invention, provision is made for the cutting jig to include a turntable arrangement with a turntable which is rotatably supported at the cutting jig and with which a guide section is rotatably fixedly connected in which the slot defining the second cutting plane is formed. The rotational axis of the turntable can extend perpendicular to the first cutting plane in this process.

Provision can furthermore be made for a further guide section to be rotatably connected to the turntable and to be formed as a guide for the abutment element. The relative position between the slot defining the second cutting plane and the guide for the abutment element can hereby be fixedly pre-determined in a simple manner.

The cutting jig can furthermore have a clamping device with an actuating member by means of which the cutting jig can be fixed relative to the base element and simultaneously the orientation of the second cutting plane can be fixed relative to the first cutting plane. The cutting jig in accordance with the invention can so-to-say hereby be fixed in the desired position simultaneously with a single motion with respect to all degrees of freedom of movement provided for the fixing of the position of the bone cuts.

The cutting jig can include a base part made in a U shape and being able to be pushed onto the base element with U limbs extending parallel to the first cutting plane, a clamping lever pivotably supported at the base part about an axis which extends parallel to the first cutting plane and perpendicular to the U limbs of the base part and a clamping spindle extending parallel to the U limbs of the base part and cooperating with the clamping lever via a thread, with a turntable arrangement rotatably supported at the upper U limb of the base part about an axis extending perpendicular to the first cutting plane and having the slot defining the second cutting plane being capable of being fixed by a rotational actuation of the clamping spindle and simultaneously the clamping lever being pivotable relative to the base part into clamping engagement with the base element.

In this process, a free end region of the clamping spindle can be made for the fixing of the turntable arrangement and can be brought into clamping engagement with an outer rim region of the turntable arrangement by rotational actuation of the clamping spindle.

Furthermore, the clamping lever can include an actuation arm and a clamping arm, with the clamping spindle cooperating with the actuating arm and the clamping arm being pivotable, for the clamping tight of the base element located between the two U limbs of the base part, by rotational actuation of the clamping spindle via the actuating arm into the region between the two U limbs and toward the base element.

An accidental release of the clamping engagement, for example due to vibrations occurring during the carrying out of the bone cuts, can be prevented in a particularly reliable manner if, in accordance with a further embodiment of the invention, cooperating thread sections of the clamping spindle and of the clamping lever are held free of clearance by a spring tensioned between a contact section fixed relative to the spindle and the actuation arm of the clamping lever.

The intermediate space between the two U limbs of the base part is preferably matched to the height of the base element.

The invention permits the use of comparatively thin base elements which, for example, have a thickness of only approximately 12 mm.

The invention will be described in the following by way of example with reference to the drawing. There are shown.

Before constructive details of the apparatus in accordance with the invention are considered with reference to FIGS. 6 to 8, that part of a knee operation should be explained with reference to FIGS. 1 to 5 in which the apparatus in accordance with the invention is used.

It is the aim of the total operation to insert a knee prosthesis consisting of a tibia implant and a femur implant. Uni-compartmental surgical procedures are above all of interest in connection with the invention by which initially a plateau is created at the respective tibial condyle by cutting away bone material for the tibia implant to be inserted, whereupon the opposite femoral condyle is likewise prepared for the fixing of a corresponding femur implant by cutting away bone material.

In this process, not only a correct positioning of the tibia implant at the tibia and of the femur implant at the femur is important, but also and quite decisively the correct alignment of the tibia implant and of the femur implant relative to one another. To ensure the correct positioning of the implants, in addition to a good surgical plan, an exact carrying out of the bone cuts required to remove the bone material is of decisive importance.

The present invention relates, in accordance with the embodiment shown in the Figures, to the fixing of the position of bone cuts to be carried out on a tibial condyle for the producing of a plateau for a tibia implant by means of a set of instruments which permits the cutting planes to be fixed while taking into account the anatomical circumstances of the respective knee before the cuts are carried out by means of cutting tools in particular provided in the form of saws.

Figure 1:
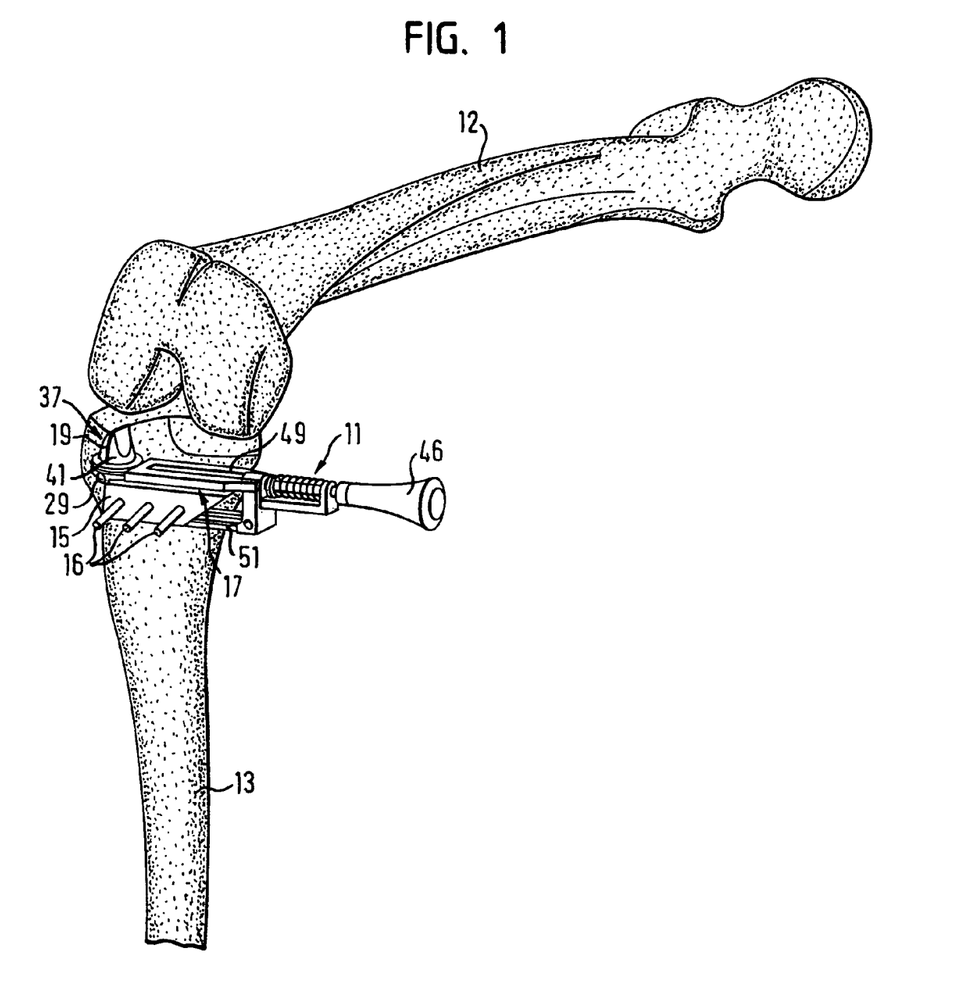
FIGS. 1 to 5 different phases of part of a knee operation in which bone cuts are carried out on a tibial condyle by means of an apparatus in accordance with the invention.

The starting point for the part of the total operation which can be carried out by means of the set of instruments in accordance with the invention is a base element 15 which is also termed a cutting block in the following and which is fixed to the tibia 13 by means of holding pins 16. The base element 15 has previously been positioned relative to the tibia 13 such that the planar upper side of the base element 15 lies at the height of the tibial plateau to be produced in accordance with the surgical plan by the position of the bone cuts to be fixed. In other words: the upper side of the cutting block 15 sets the position and orientation of that cutting plane relative to the tibia 13 which is also termed the first cutting plane in the following.

However, the cutting depth with which this first bone cut has to be carried out in the direction lateral-medial is thus not yet known to the surgeon. It is likewise not known to the surgeon how the second bone cut inwardly bounding the tibial plateau should be orientated relative to the tibia and thus to the first cutting plane. Both the optimum depth of the first cut in the direction of the cruciate ligaments and of the eminentia and the optimum orientation of the second cut along the cruciate ligaments and along the eminentia depend on the respective knee anatomy and previously had to be fixed by the surgeon during the operation without any aids and thus only "by feel".

This is where the invention comes in. First, a cutting jig 11 is pushed onto the cutting block 15 with a U-shaped base part. The base part includes an upper U limb 49 and a lower U limb 51. The lower U limb 51 of the cutting jig 11 is guided in a groove, for example a T-shaped groove, formed at the lower side of the cutting block 15 such that the cutting jig 11 can only be moved in the plane fixed by the upper side of the cutting block 15 and parallel to the guide groove of the cutting block 15, i.e. parallel to the U limbs 49, 51 relative to the cutting block 15.

The cutting jig 11 defines a first cutting plane for a first bone cut by means of a slot-shaped intermediate space 17 between the upper U limb 49 and the upper side of the base element 15. In this process, the slot 17 serves as a guide for the cutting tool provided as a saw blade in order to carry out this horizontal cut.

A second slot 19 extending perpendicular to the first slot 17 is formed in a turntable arrangement 37 of the cutting jig 11. The turntable arrangement 37 permits the orientation of the second slot 19 to be set relative to the cutting plane defined by the first slot 17.

A threaded spindle 45 provided with a handle 46 permits the turntable arrangement 37 to be fixed in the respectively set orientation and the cutting jig 11 to be simultaneously fixed to the base element 15. This fixing of the cutting jig 11 and of the turntable arrangement 37 takes place when the optimum orientation of the cutting plane fixed by the second slot 19 has been found.

Figure 2:
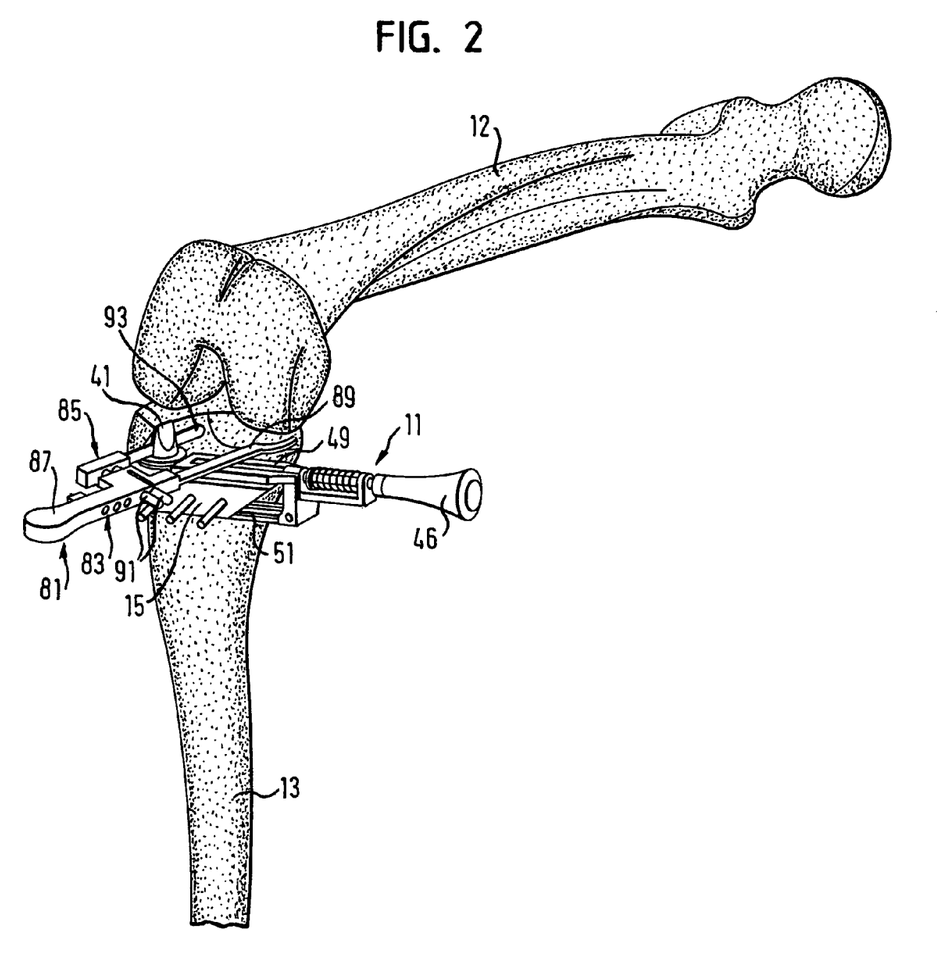

To find the optimum orientation of the second vertical cutting plane, a probe device 81 is coupled to the cutting jig 11. The probe device 81 has a base part 85 with a strip-shaped coupling section 93 which is inserted into the slot 19 of the turntable arrangement 37 in order to establish a compulsory coupling between the probe device 81 and the slot 19 defining the second cutting plane. Consequently, the probe device 81 can be rotated via the coupling section 93 of the base part 85 as a whole relative to the cutting jig 11 and thus relative to the tibia 13 about an axis extending perpendicular to the cutting plane defined by the first slot 17.

A further degree of freedom of movement of the probe device 81 is provided by a probe including an actuation section 87 and a probe arm 89 which is longitudinally displaceably guided parallel to the first cutting plane on two guide pins 91 connected to the base part 85. The probe 83 can be latched to one of the guide pins 91 in different positions which each correspond to a pre-determined implant size.

After pushing the cutting jig 11 onto the cutting block 15 and the insertion of the coupling section 93 into the rotatable slot 19 of the cutting jig 11, the optimum orientation of the second cutting plane fixed by the slot 19 can be probed by displacing the coupling section 93 in the mediolateral direction and by rotating the probe device 81 relative to the cutting jig 11 and fixed by the handle. In a further step, the correct size of the implant relative to the outer edge can be determined by the surgeon on the tibia by displacing the probe 83 along the guide pins 91 and by moving the probe device along the second cutting plane. With an implant size determined in this manner, a fine correction can still be carried out at any time by a short-term release and renewed tightening of the handle 46.

In this process, the surgeon can grip the actuation section 87 of the probe device 81 with the one hand and the handle 46 of the cutting jig 11 with the other hand and thus bring the total arrangement of cutting jig 11 and probe device 81 into a configuration taking the anatomical circumstances of the respective knee into optimum account in accordance with the given degrees of freedom of movement.

The surgeon determines the optimum configuration by probing by means of the coupling section 93 and of the probe arm 89 and by a visual check of the position of the coupling section 93 and of the probe arm 89 relative to the tibia 13. To facilitate the visual check, the free end of the probe arm 89 is curved in accordance with the outer lateral boundary of the later implants.

When the optimum configuration of the set of instruments in accordance with the invention and thus the optimum orientation of the second cutting plane as well as the best suitable implant size has been set, the turntable arrangement 37 provided with the slot 19 is fixed with respect to the cutting jig 11 and the cutting jig 11 is fixed with respect to the cutting block 15 by rotating the thread spindle via the handle 46. The probe device 81 is then removed.

Subsequently—guided via a passage 29 likewise formed at the turntable arrangement 37 and aligned with the slot 19 (cf. FIG. 1)—a bore is formed in the bone into which an abutment pin 31 guided in the passage 29 is then inserted (cf. FIG. 3). The passage 29 serving as a guide both for the drilling tool and for the abutment pin 31 is oriented such that its central axis extends parallel to the imagined sectional line between the first slot 17 and the second slot 19 and such that its longitudinal section covers the prolongation of the slots 17, 19 as completely as possible. Consequently, the abutment pin 31 introduced into the bone through the passage 29 serves as an abutment bounding both the first cut and the second cut for the saw blades guided through the slots 21, 23 (cf. FIGS. 3 and 4).

Figure 3:
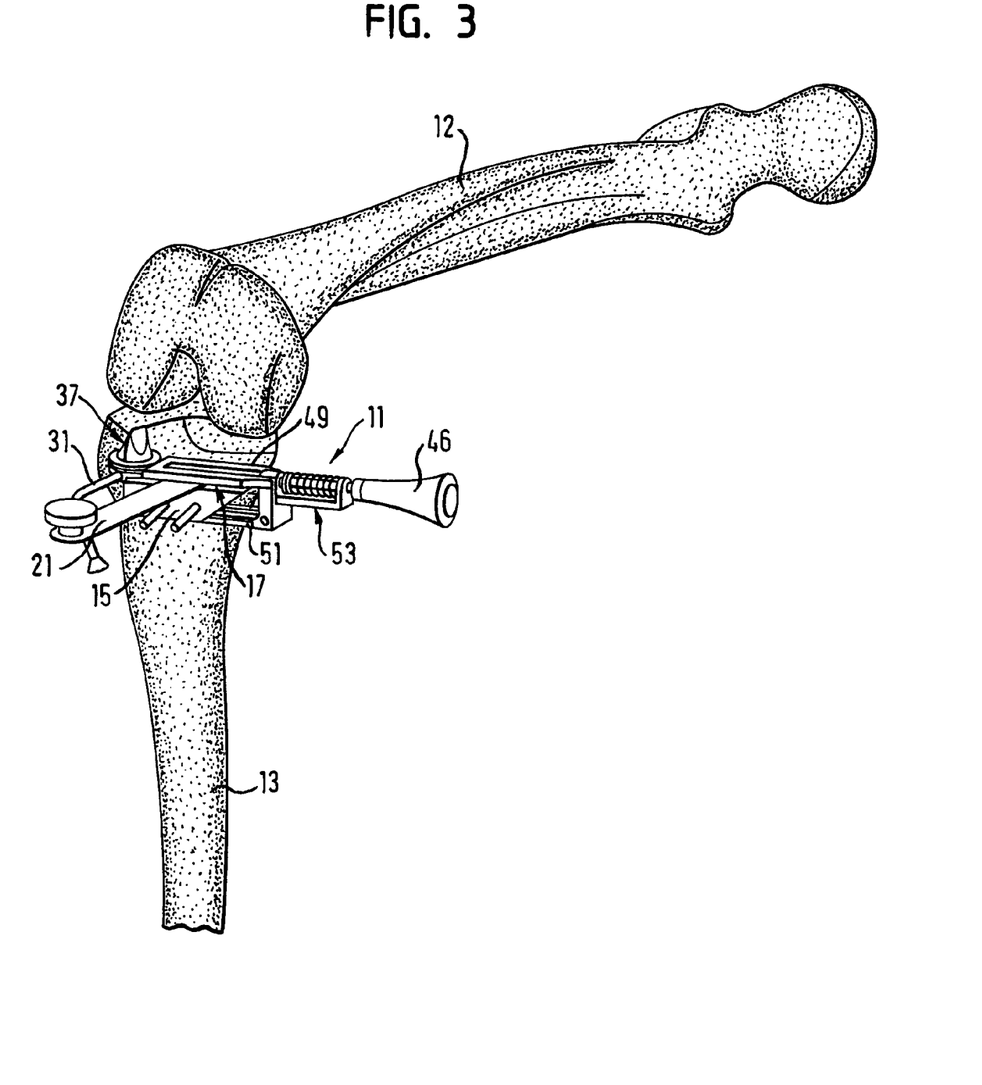
Figure 4:
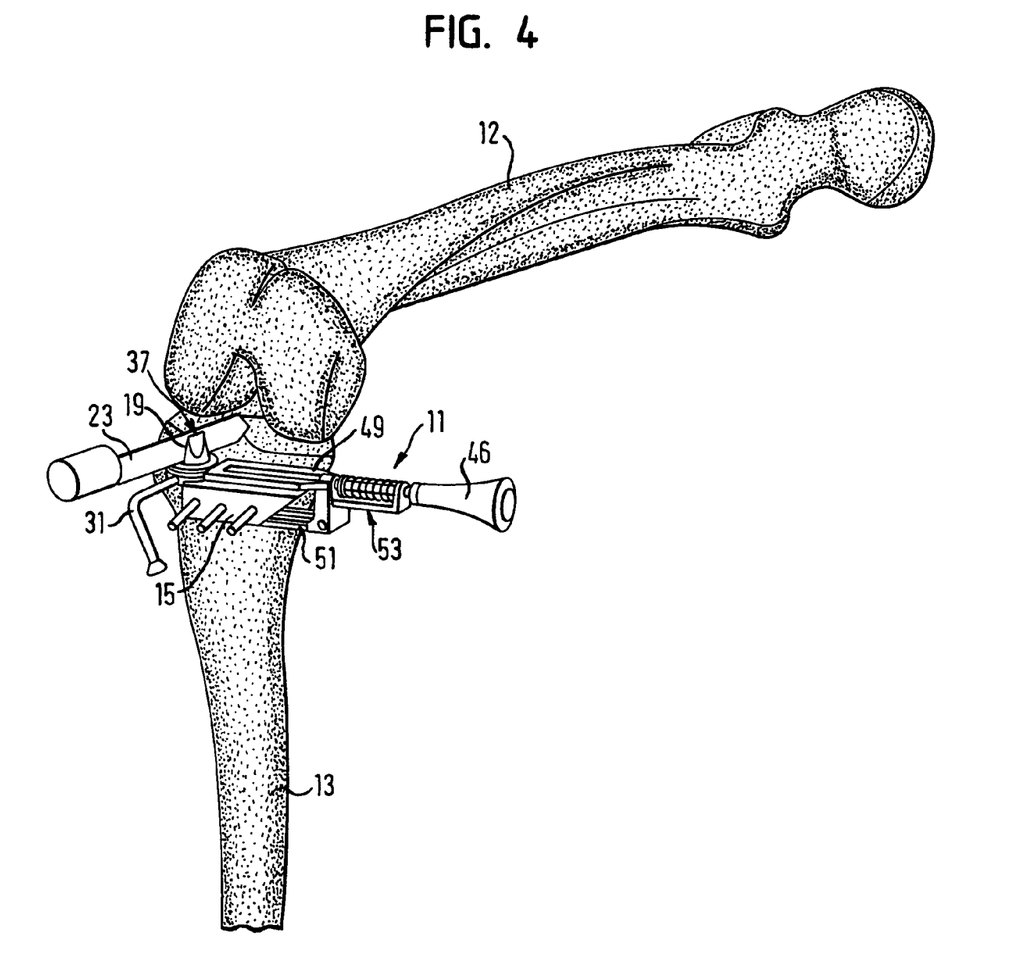

After the insertion of the abutment pin 31 into the bone, first, in accordance with FIG. 3, the first cut is carried out by means of the saw blade 21 guided through the first slot 17 and its depth is bounded by the abutment pin 31 in the direction of lateral-medial. Subsequently, in accordance with FIG. 4, a second cut extending perpendicular to the first cut is carried out by means of the saw blade 23 guided through the second slot 19 and its depth is likewise bounded by the abutment pin 31 in the distal direction.

Figure 5:
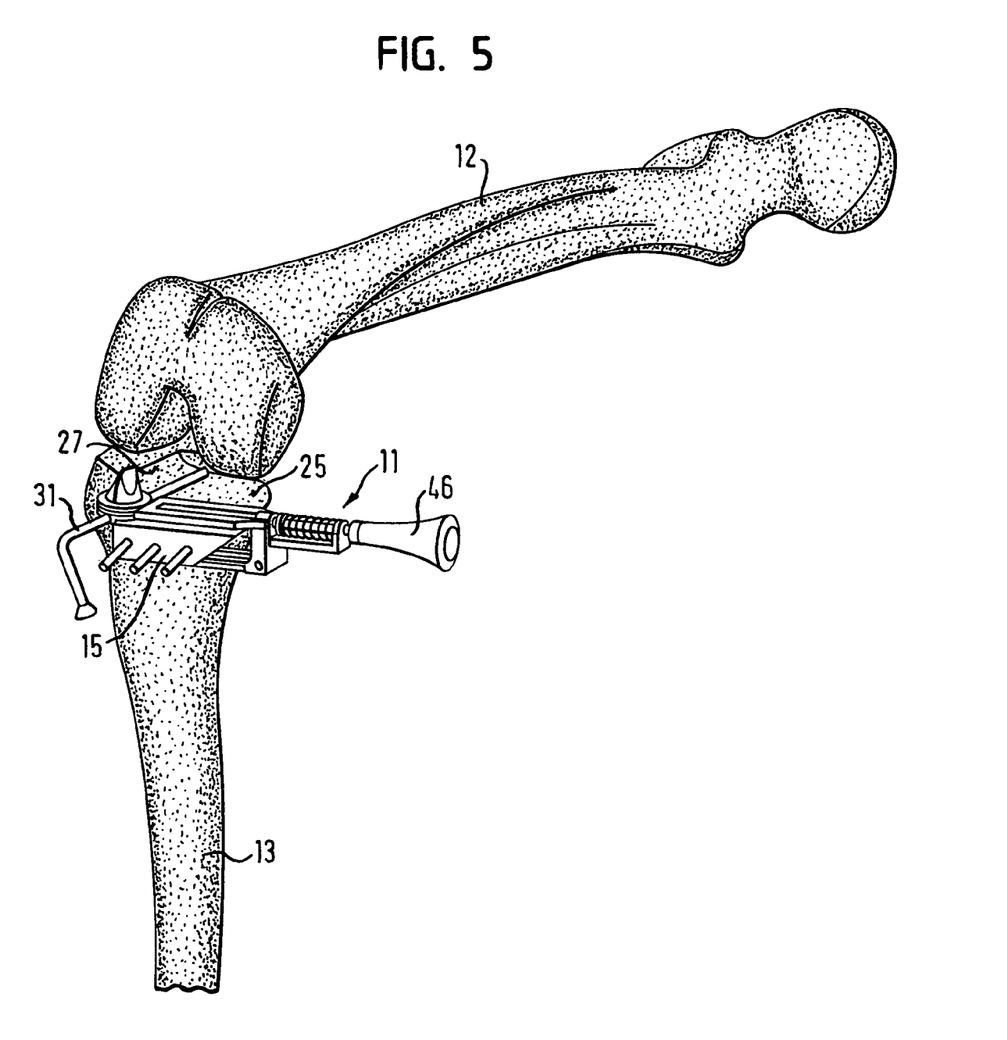

FIG. 5 shows the tibia plateau created by means of the set of instruments in accordance with the invention and bounded by cut surfaces 25, 27 extending perpendicular to one another, with moreover the abutment pin 31 coinciding with the line of intersection of the two cut surfaces 25, 27 being shown.

Subsequently, the abutment pin 31 is pulled out, the clamping of the cutting jig 11 at the cutting block 15 is canceled and the cutting jig 11 is removed from the cutting block 15. The tibia 13 is thus prepared for the insertion of the tibia implant of the knee prosthesis, with the opposite femoral condyle, however, having been prepared previously, with this, however, not being looked at in detail.

Figure 6:
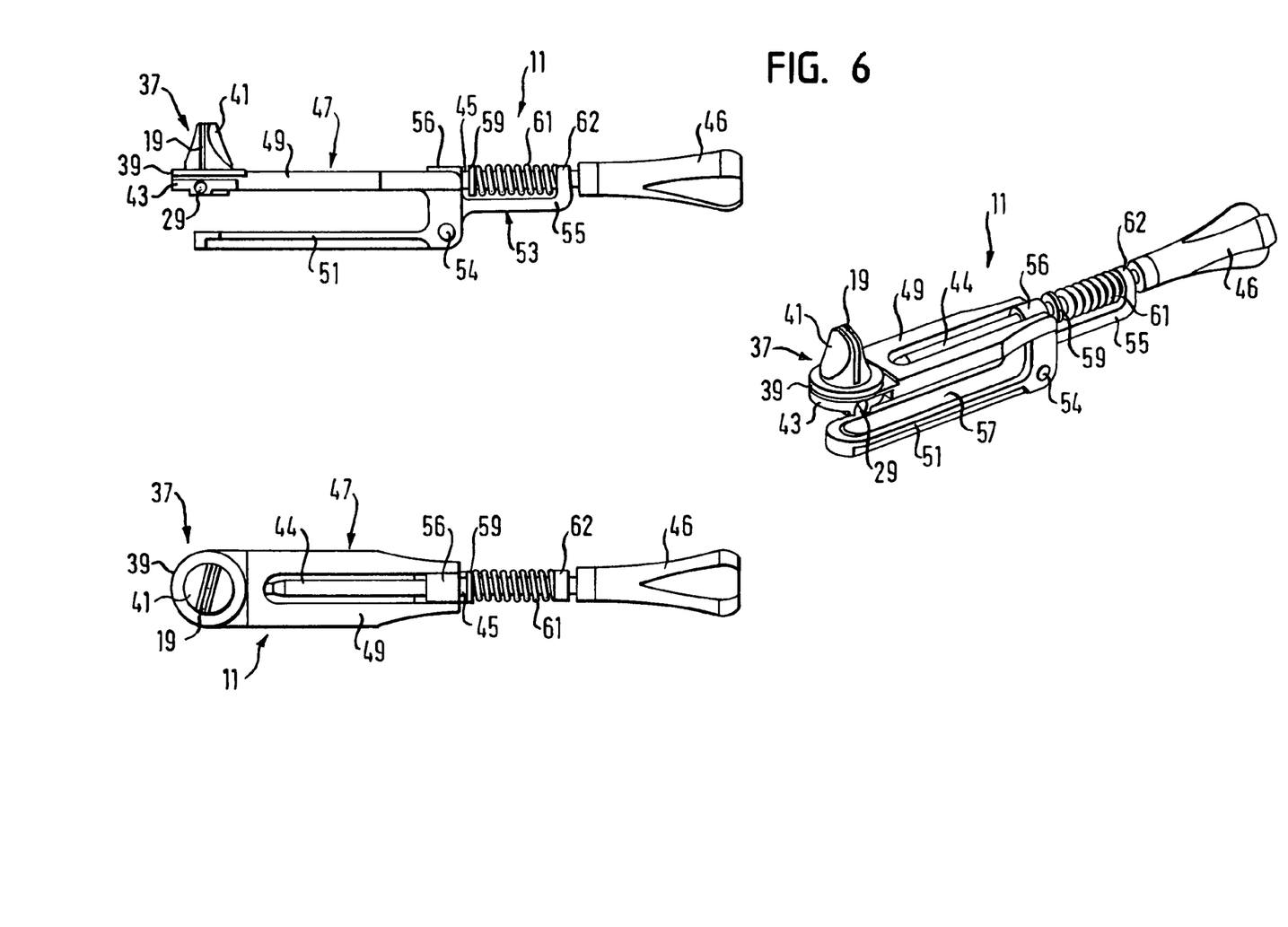
FIG. 6 different views of a cutting jig in accordance with an embodiment of the invention.

In accordance with FIG. 6, the cutting jig 11 in accordance with the invention includes the U-shaped base part 47 with the two U limbs 49, 51 extending in parallel. The free end of the upper U limb 49 supports the turntable arrangement 37 which includes a turntable 39 rotatably supported at the upper U limb 49 and an upper guide section 41 provided with the slot 19 and a lower guide section 43 provided with the passage 29. The guide sections 41, 43 are rotatably fixedly connected to the turntable 39. The passage 29 is aligned with the slot 19, i.e. the central axis of the passage 29 lies in the cutting plane defined by the slot 19.

A clamping lever 53 is pivotably supported on the base part 47 via a pin 54 about an axis extending perpendicular to the two U limbs 49, 51. The clamping lever 53 includes a clamping arm 57 and an actuation arm 55 which extend in parallel offset to one another. The clamping arm 57 formed in the manner of a tongue extends in a correspondingly shaped recess of the lower U limb 51 and can be pivoted into the region between the two U limbs 49, 51 by pivoting of the clamping lever 53.

The clamping lever 53 furthermore includes a thread section 56 which is provided with an internal thread and which cooperates with a clamping spindle 45 having a corresponding external spindle. The spindle 45 extends in the one direction through a guide opening which is formed in a support and guide section 62 formed by the free end region of the actuation arm 55 of the clamping lever 53. The clamping spindle 45 is provided at its free end with the handle 46. The clamping spindle 45 extends in the opposite direction in the form of a pin-shaped clamping section 44 whose free end (not shown) can be brought into clamping engagement with an outer rim region of the turntable arrangement 37 when the spindle 45 is rotated in the corresponding direction.

A pressure spring 61 is clamped between a support section 59 fixedly connected to the spindle 45 and the support and guide section 62 and holds the external thread of the spindle 45 and the internal thread of the threaded section 56 of the clamping lever 53 without clearance in every position of the spindle 45.

By rotating the spindle 45, the free end of the clamping section 44 of the spindle 45 is moved in the direction of the turntable arrangement 37 and finally into clamping engagement with the turntable arrangement 37, whereby the turntable arrangement 37 is fixed relative to the base part 47. As soon as the spindle 45 is prevented from further axial movement by the turntable arrangement 37, a turning further of the spindle 45 results in an axial movement of the threaded section 56 of the clamping lever 53 away from the turntable arrangement 37 and thus in a pivoting of the clamping lever 53, which has the consequence that the clamping arm 57 of the clamping lever 53 moves in the direction of the upper U limb 49 of the base part 47 and thus into the intermediate space between the two U limbs 49, 51.

As already explained above in connection with FIGS. 1 to 5, the actuation of the clamping device including the clamping spindle 45 and the clamping lever 53 takes place with the cutting jig 11 pushed onto the cutting block 15, i.e. the cutting block 15 is located in the intermediate space between the two U limbs 49, 51. A relatively small pivot movement of the clamping lever 53 is therefore sufficient in order to fix the cutting jig 11 at the cutting block 15 via the clamping arm 57 coming into clamping engagement with the lower side of the cutting block 15.

The turntable arrangement 37 can thus be both fixed and released again with respect to the base part 47 of the cutting jig 11 and the cutting jig 11 can be both fixed and released again with respect to the cutting block 15 simultaneously by actuation of the spindle 47 via the handle 46.

Figure 7:
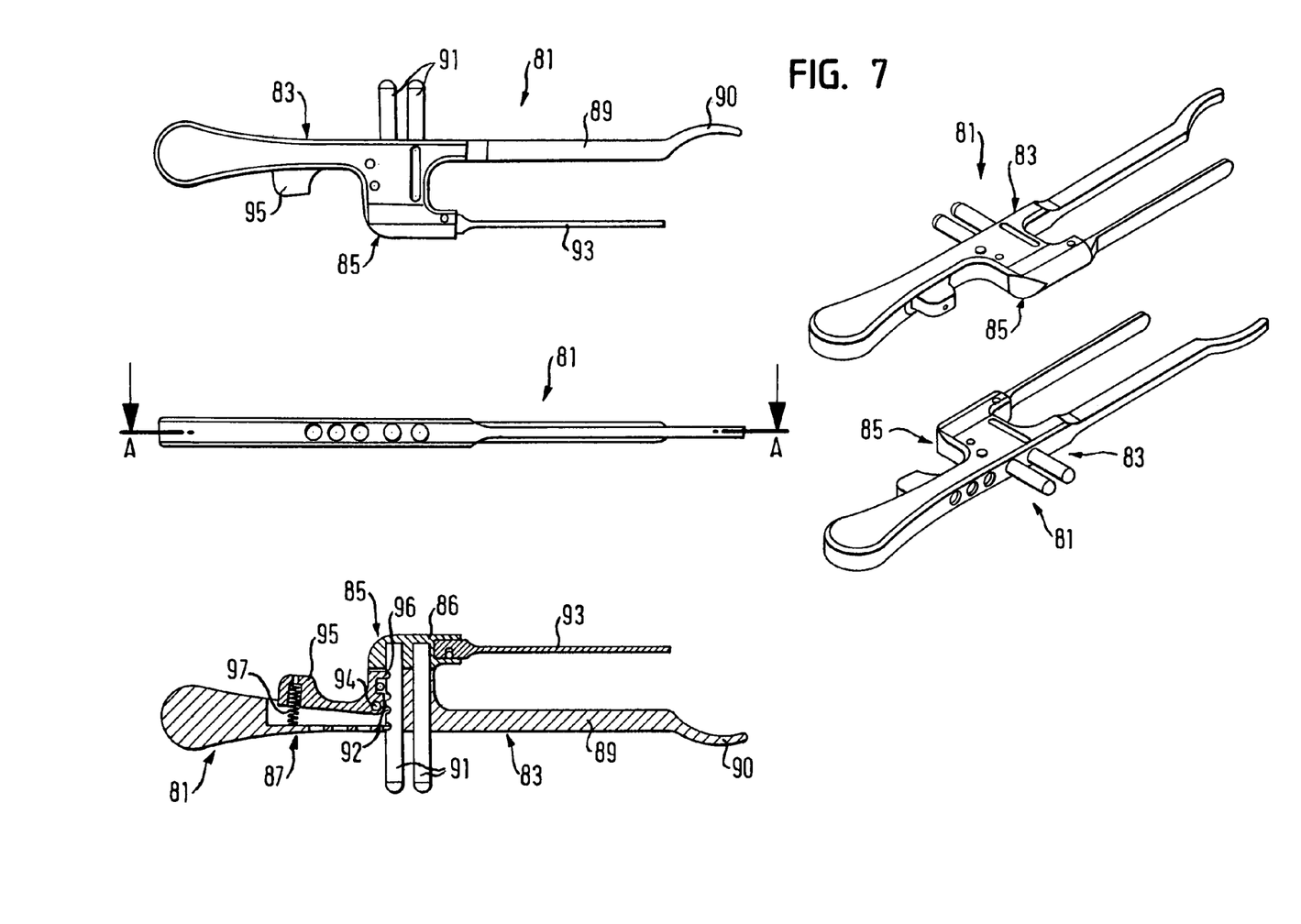
FIG. 7 different views of a probe device in accordance with an embodiment of the invention which can be used with the cutting jig of FIG. 6.

In accordance with FIG. 7, the base part 85 of the probe device 81 includes a support 86 with which the strip-shaped coupling section 93, on the one hand, and the two guide pins 91 for the probe 83 displaceable relative to the base part 85 along the guide pins 91, on the other hand, are connected.

The probe 83 includes the probe arm 89 having the curved free end 90 and extending parallel to the coupling section 93 as well as an actuation section 87 at which an actuation lever 95 is pivotably supported via a pin 94. A latching nose 96 of the one lever arm of the actuation lever 95 is biased toward the one guide pin 91 by a restoration spring 97 acting on the other lever arm of the actuation lever 95 and supported at the actuation section 87 such that, with an appropriate relative position between the base part 85 and the probe 83, the latching nose 96 engages into recesses formed at this guide pin 91, whereby the relative position between the base part 85 and the probe 83 is fixed. The positions of the latch recesses of the guide pin 91 correspond to the sizes of tibia implants of an existing set of implants.

The surgeon holding the probe device 81 coupled to the cutting jig 11 (cf. FIG. 2) at the actuation section 87 can release the latching of the probe 93 at the guide pin 91 by actuating the lever 95 against the restoring force of the spring 97 and can set all pre-determined implant sizes at the probe device 81 by displacing the probe 83 along the guide pins 91 relative to the base part 85 and can in this manner determine the best matched implant size for the knee while taking the anatomical circumstances of the respective knee into account.

Figure 8:
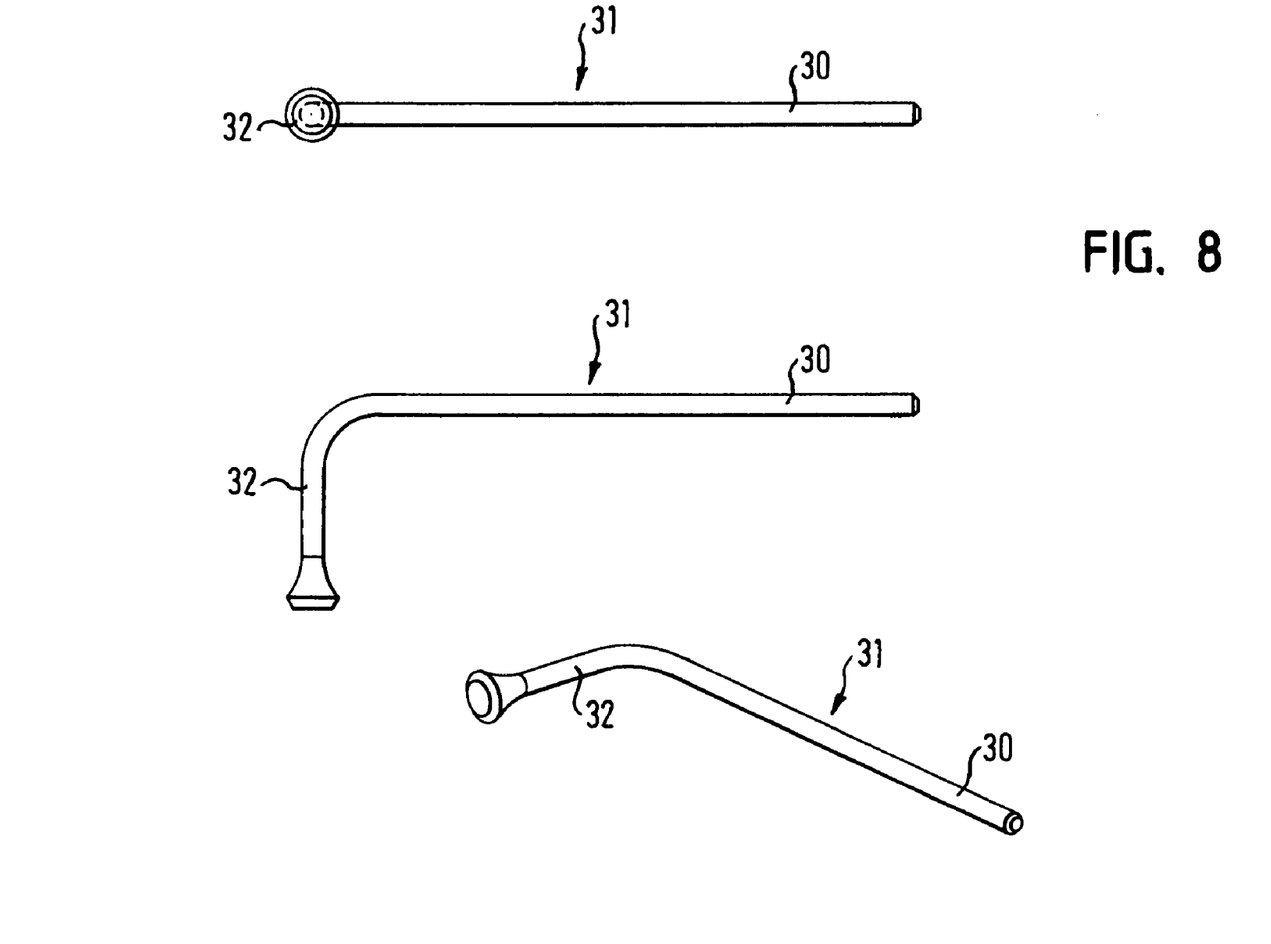
FIG. 8 different views of an abutment element in accordance with an embodiment of the invention which can be used with the cutting jig of FIG. 6.

The abutment pin 31 shown in FIG. 8 (cf. also FIGS. 3 to 5) includes a straight abutment section 30 with which the abutment pin 31 is inserted through the passage 29 formed at the turntable arrangement 37 of the cutting jig 11 into the bore previously formed in the bone as well as a holding section 32 angled by 90° at which the surgeon can grip the abutment pin 31 on the insertion into the bone and on the pulling out from the bone. The free end of the holding section 32 is provided with a radial extension. The abutment pin consists of a hardened metal alloy so that no wear occurs on the lateral bounding of the saw blades. It is angled so that it cannot be confused with customary straight pins.

REFERENCE NUMERAL LIST

11 cutting jig
12 femur
13 tibia
15 base element, cutting block
16 holding pin
17 first slot
19 second slot
21 first cutting tool, first saw blade
23 second cutting tool, second saw blade
25 first cutting plane, first cutting surface
27 second cutting plane, second cutting surface
29 guide, passage
30 abutment section
31 abutment element, abutment pin
32 holding section
33 intersection line of the cutting planes 37 turntable arrangement
39 turntable
41 guide section
43 guide section
44 clamping section
45 actuation member, clamping spindle
46 handle
47 base part
49 upper U limb
51 lower U limb
53 clamping lever
54 pin
55 actuation arm
56 threaded section
57 clamping arm
59 support section
61 spring
62 support and guide section
81 probe device
83 probe
85 base part
86 support
87 actuation section
89 probe arm
90 curved free end
91 guide pin
92 latch recess
93 coupling section
94 pin
95 actuation lever
96 latching nose
97 restoration spring

The invention claimed is:

1. An apparatus for the fixing of the position of bone cuts for the insertion of knee implants, the apparatus comprising:
   a base element adapted to be fixed to a bone in the region of a condyle; and
   at least one cutting jig adapted to be coupled to the base element, the cutting jig comprising:
      a first slot for guiding a cutting tool, the first slot defining a first cutting plane with respect to the base element, the first slot configured to receive a cutting tool while the cutting jig remains coupled to the base element;
      a U-shaped base part having a pair of U limbs, wherein, when the cutting jig is coupled to the base element, the pair of U limbs are parallel to the first cutting plane and at least a portion of the base element is received between the pair of U limbs;
      a clamping lever pivotably supported at the U-shaped base part about an axis extending parallel to the first cutting plane and perpendicular to a longitudinal axis of the U limbs;
      a clamping spindle extending parallel to the U limbs of the U-shaped base part and cooperating with the clamping lever via a thread; and
      a turntable arrangement rotatably supported by one of the pair of U limbs, the turntable arrangement rotatable about an axis extending perpendicular to the first cutting plane, the turntable arrangement defining a second slot for guiding a cutting tool, the second slot configured to receive a cutting tool while the cutting jig remains coupled to the base element and while taking the respective knee anatomy into account, wherein the rotational position of the second slot relative to the first slot is fixed by rotational actuation of the clamping spindle and the clamping lever is simultaneously pivotable relative to the U-shaped base part to clampingly engage the base element.

2. The apparatus of claim 1, wherein the clamping spindle further comprises a free end region configured for fixing the rotational position of the turntable arrangement, wherein rotational actuation of the clamping spindle brings the free end region of the clamping spindle into clamping engagement with an outer rim region of the turntable arrangement.

3. The apparatus of claim 1, wherein the clamping lever comprises an actuation arm and a clamping arm, wherein the clamping spindle cooperates with the actuation arm to pivot the clamping arm when the clamping spindle is rotated, wherein, with at least a portion of the base element received between the pair of U limbs, rotational actuation of the clamping spindle results in corresponding pivoting of the clamping lever via the actuation arm to clamp the cutting jig to the base element.

4. The apparatus of claim 3, wherein cooperating threaded sections of the clamping spindle and of the clamping lever are held free of clearance by a spring clamped between a contact section fixed with respect to the spindle and the actuation arm of the clamping lever.

5. The apparatus of claim 1, wherein an immediate space between the pair of U limbs of the base part is matched to the height of the base element and is designed for a base element with a height of approximately 12 mm.

* * * * *